US006678764B2

(12) United States Patent  
Parvulescu et al.

(10) Patent No.: US 6,678,764 B2
(45) Date of Patent: Jan. 13, 2004

(54) MEDICAL IMAGE PROCESSING SYSTEM (75) Inventors: Adrian Parvulescu, Fishs Eddy, NY (US); Robert P. Ellis, Warwick, NY (US)

(73) Assignees: Sony Corporation, Tokyo (JP); Sony Electronics, Inc., Park Ridge, NJ (US)

( * ) Notice: Subject to any disclaimer, the term of this patent is extended or adjusted under 35 U.S.C. 154(b) by 297 days.

(21) Appl. No.: 09/870,270

(22) Filed: May 30, 2001

(65) Prior Publication Data

US 2002/0080392 A1 Jun. 27, 2002

Related U.S. Application Data (60) Provisional application No. 60/241,948, filed on Oct. 20, 2000.

(51) Int. Cl.$^7$ .............................................. G06F 13/12
(52) U.S. Cl. ......................... 710/65; 600/407; 707/10; 382/128
(58) Field of Search ........................... 710/65; 600/407; 707/10

(56) References Cited

U.S. PATENT DOCUMENTS

| | | | | |
|---|---|---|---|---|
| 5,920,317 A | * | 7/1999 | McDonald | 345/356 |
| 6,188,782 B1 | * | 2/2001 | Le Beux | 382/128 |
| 6,241,668 B1 | * | 6/2001 | Herzog | 600/407 |
| 6,529,757 B1 | * | 3/2003 | Patel et al. | 600/407 |
| 6,574,629 B1 | * | 6/2003 | Cooke, Jr. et al. | 707/10 |

OTHER PUBLICATIONS

"Installation and User Guide" for Sony UP-D70XR, 3 pages, Apr. 10, 200, (See Appendix item #1).
Sony DKR-700 Digital Camera, two Internet Postings, product released in 1997 (See Appendix item #2).
"Stryker Digital Capture", Product data sheet from Internet, Desktop Medical, 1998 (See Appendix item #3).

TEAC MV-180—No published information located (See Appendix item #4 for technical information).

TEAC Viewfile MC-71—Product Specification, two pages, Jun. 2001 (See Appendix item #6).

TEAC MV-300N—Product specification, six pages undated. (See Appendix item #5).

TEAC MV-300P—Product specification, six pages undated. (See Appendix item #5).

Visiplex CCM601—Product specification, two pages, Sep. 1996, (See Appendix item #7).

Visiplex CCM200—Product specification, two pages, 1993, (See Appendix item #7).

Visiplex CCM620—Product specification, one page, undated, (See Appendix item #7).

* cited by examiner

Primary Examiner—Abdelmoniem Elamin
(74) Attorney, Agent, or Firm—Miller Patent Services; Jerry A. Miller (57) ABSTRACT A medical image archiving system and method. A medical image archiving system receives analog NTSC or PAL video from a medical imaging device and converts it to a digital format for storage. The storage can be via local hard disc drive, or CD writer, or other optical storage medium, or via Local or Wide area network storage to a remote electronic storage medium. The system includes an integral web server to permit easy access over a network using a browser. When an image is stored on a CD, it can be stored as a session and the CD closed to prevent further writing.

21 Claims, 7 Drawing Sheets

Hospital/Unit Name: [County Memorial / Cardiac]
Matrix: ○2X2 ●2X3  Video: ●NTSC ○PAL
Color: ●Color ○Mono  Input Port: ●Composite ○S-Video
Terminal Support: ☑
CD Recorder Support: ☑  ●Single session ○Multi-session
Video Printer Support: ☑
IP Address: [43.136.17.248]  Netmask: [255.255.255.0]  Gateway: [43.136.17.3]
Expiration Time (days): [3]
Doctor's Name: ●Always Ask ○Never Ask ○Use Default
Default Name: [Staff Doctor]
Procedure Name: ●Always Ask ○Never Ask ○Use Default
Default Name: [Procedure]
Time Zone: [Africa/Abidjan ▼]  Date/Time: [2001/05/05] [15:23]  SetDate: ☐  Save Config. — 704
Language: [English ▼]  Reboot ☐  Start Over — 708

MEDICAL IMAGE PROCESSING SYSTEM

This application claims the benefit of provisional application Ser. No. 60/241,948 filed Oct. 20, 2000.

FIELD OF THE INVENTION

This invention relates generally to medical image systems, and more particularly to a medical image archiving and information exchange system, with image management features.

BACKGROUND OF THE INVENTION

The medical community currently relies heavily upon a large installed base of tens of thousands of analog medical imaging devices (for example, ultrasound imaging devices) that provide no inherent capability to provide persistent storage of the images produced. Additional hardware is required to produce persistent images. Some of the most prevalent of such hardware are devices using a camera and a CRT display coupled by an optical system. The user sends analog video signals to this device and the device produces a hard copy in the form of an x-ray type picture or photo quality print of images made by the imaging device. This camera-type imager contains a conventional film camera mechanism. This camera mechanism inside the camera imager is moved mechanically to produce formats of 1, 4, 6, or 9 images on a single sheet of film. The film is then processed using an X-ray film processor so that the resultant hard copy image can be made a part of a patient's paper medical records. To utilize such a system requires the camera imager, the auto X-ray film processor, and the chemicals for the developer and the fixer, which require constant replenishment. This system does not provide for ready electronic storage and transfer of the images for convenient archiving or for rapid and convenient examination by a consulting physician located in a distant part of a hospital or even in another city. Moreover, the system requires technical skills in developing the resulting images, and has proven expensive to use and maintain. Such devices are commercially available.

Several other devices have been used in the marketplace to capture images on paper or on proprietary electronic media, but none have proven very commercially successful. Proposed standards such as HIPPA (Health Insurance Portability and Accountability Act) are likely to place strict requirements on the archiving of medical records in the near future. This places a substantial burden on hospitals, clinics and doctors which may not be adequately met with current archiving systems.

SUMMARY OF THE INVENTION

The present invention relates generally to medical imaging. Objects, advantages and features of the invention will become apparent to those skilled in the art upon consideration of the following detailed description of the invention.

In one embodiment of the present invention, a medical image archiving system and method is provided. A medical image archiving system receives analog NTSC or PAL video from a medical imaging device and converts it to a digital format for storage. The storage can be via local hard disc drive, or CD writer, or other optical storage medium, or via Local or Wide area network storage to a remote electronic storage medium. The system includes an integral web server to permit easy access over a network using a browser. When an image is stored on a CD, it can be stored as a session and the CD closed to prevent further writing.

A medical imaging method consistent with an embodiment of the present invention includes receiving an analog video input signal from a medical imaging device; converting a frame of the analog video input signal to a digital representation; assigning a file name to the digital representation; storing the digital representation on a disc drive; and storing the digital representation as a part of a session on an optical storage medium.

A medical image archiving device, consistent with an embodiment of the present invention includes a frame grabber that receives an analog video image from a medical imaging device and produces a digitized still image in response to a command. A programmed processor is connected to a network interface adapter that interfaces the processor to an electronic communication network. A web server application runs on the programmed processor, the web server having an IP address associated therewith. A disc drive stores the digitized still image. An application program running on the programmed processor receives a request directed to the IP address for the digitized still image from the network via the network interface adapter, and generates a reply transmitting the digitized image to an IP address associated with the request.

A storage medium consistent with an embodiment of the invention stores instructions which, when executed on a programmed processor, carry out a process of: receiving an analog video input signal from a medical imaging device; converting a frame of the analog video input signal to a digital representation; assigning a file name to the digital representation; storing the digital representation on a disc drive; and storing the digital representation as a part of a session on an optical storage medium. In one variation, the the digital representation is transmitted over either a wide area network or a local area network.

The above summaries are intended to illustrate exemplary embodiments of the invention, which will be best understood in conjunction with the detailed description to follow, and are not intended to limit the scope of the appended claims.

BRIEF DESCRIPTION OF THE DRAWINGS

The features of the invention believed to be novel are set forth with particularity in the appended claims. The invention itself however, both as to organization and method of operation, together with objects and advantages thereof, may be best understood by reference to the following detailed description of the invention, which describes certain exemplary embodiments of the invention, taken in conjunction with the accompanying drawings in which:

DETAILED DESCRIPTION OF THE INVENTION

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals are used to describe the same, similar or corresponding parts in the several views of the drawings.

Figure 1:
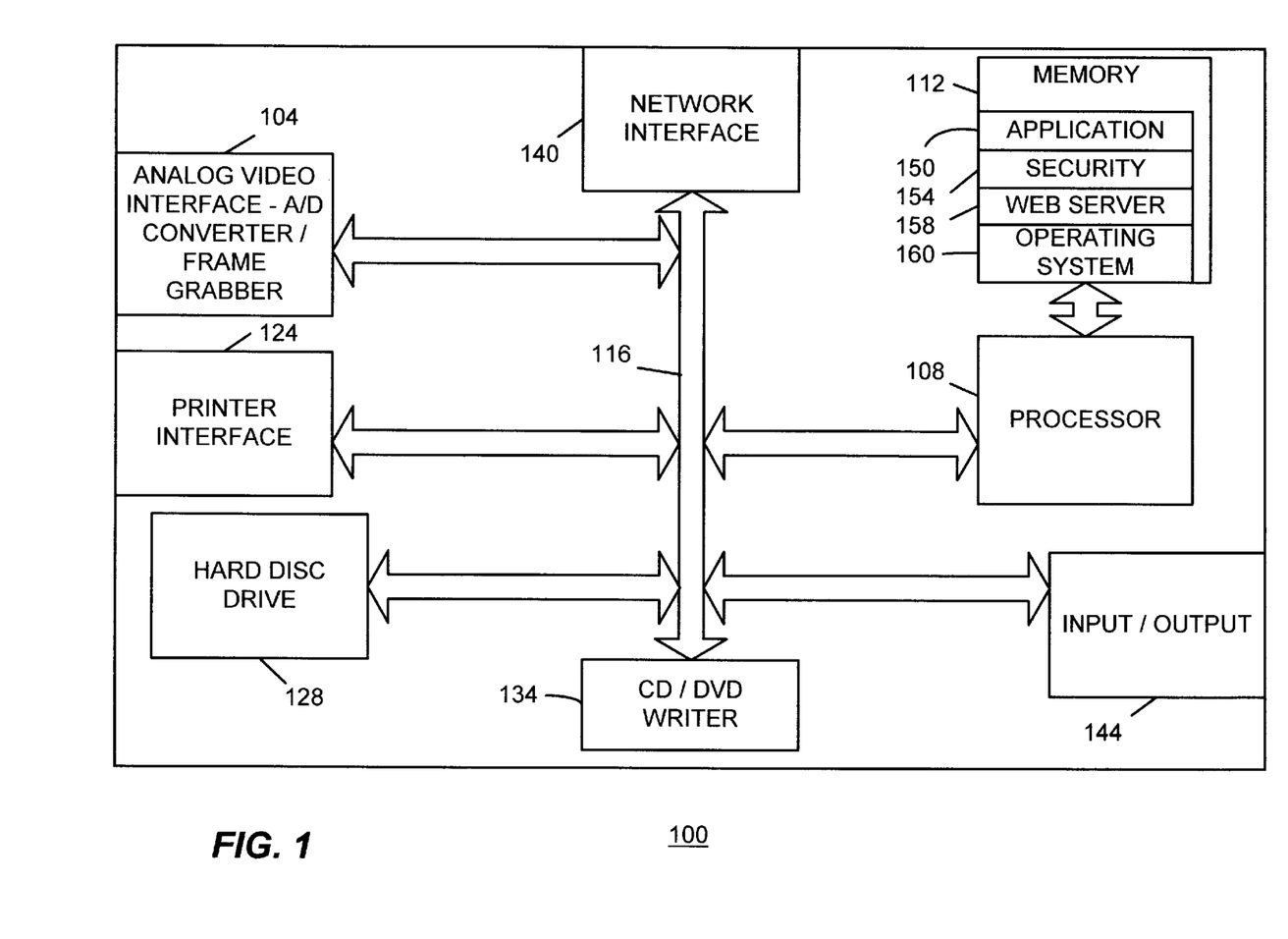
FIG. 1 is a block diagram of a medical image archiving device consistent with an embodiment of the present invention.

Turning now to FIG. 1, a medical image archiving device 100 that can be used as a part of a system to capture video images is illustrated. Once the images are generated in analog form by the medical imaging device, they can be readily converted to digital form by the current medical image archiving device 100 and archived to any suitable local or remote electronic storage medium, transferred to a remote display via a local or wide area network (including the Internet) or printed as required. Operation of the device will be best understood upon consideration of the discussions of the possible system environments to be described later. Device 100 accepts a conventional analog output (e.g., from an ultrasound imaging device) at an interface 104. This interface may receive, for example, NTSC or PAL formatted analog video signals from a medical imaging device such as an ultrasound machine and convert them to a digital format using an analog to digital converter under the control of a processor 108 (e.g., a PC based computer processor having associated memory 112). A digitally encoded still image is made available to a system bus 116 by the hardware or software based frame grabber forming a part of interface 104.

On instruction from processor 108, the image captured by the frame grabber of 104 can be output to a printer via a printer interface 124, or stored on a hard disc drive 128 or a writeable CD ROM or DVD via CD or DVD writer (media writer) 134. In alternative embodiments the media writer 134 may be provided externally to device 100 using, for example, a SCSI interface that can be used to interface to any suitable storage medium. The image can also be sent to other locations via a network interface 140 (e.g., a standard PC Ethernet interface card). Input commands from a user can be received via conventional input devices such as a footswitch, keyboard, hand held terminal, front panel controls, mouse, etc. connected to the input/output interface 144 in a conventional manner. Various conventional recordable CD drives may be used in conjunction with the image archiving device, such as a Sony™ CRX-160-E, Sony Corporation, Tokyo, Japan.

Preferably, the image signal is received at the interface 104 as a conventional (e.g., NTSC or PAL) video signal output by a conventional medical imaging device, such as an ultrasound scanning device or operating room endoscope that displays on a CRT using NTSC standards or the like. Optionally, an RGB or other analog format input may be accommodated. In one embodiment, a MATROX Meteor-II™ video capture board, as manufactured by Matrox Electronic Systems, 1055 St. Regis, Dorsal, Quebec, Canada H9P 2T4 may be used to implement the video capture functionality of interface 104. The medical image archiving device 100 captures a still image frame corresponding to the incoming video stream using the frame grabber of interface 104, and then converts the grabbed frame into a digital format under the control of processor 108. Such conversion may take place in the frame grabber interface board 104 or may be carried out by processor 108 under program control. Preferably, the .tif format is used, however, other formats could equally well be used, such as the DICOM (digital imaging and communications in medicine) format without departing from the invention. Depending upon input instructions, the grabbed and formatted image can then be stored on a local hard disc drive 128 (e.g., a 60 GB hard disc drive), recorded on a writable compact disc or the like at 134, printed via printer interface 124, or transmitted to other nodes on any network to which the device is connected via the network interface 140.

The processor 108 carries out instructions stored in memory 112 of an application 150 as will be described later. Memory 112 also stores security applications 154, a web server 158 and an operating system 160. In addition, working memory is available for use by the processor 108 to facilitate operation in a known manner.

Figure 2:
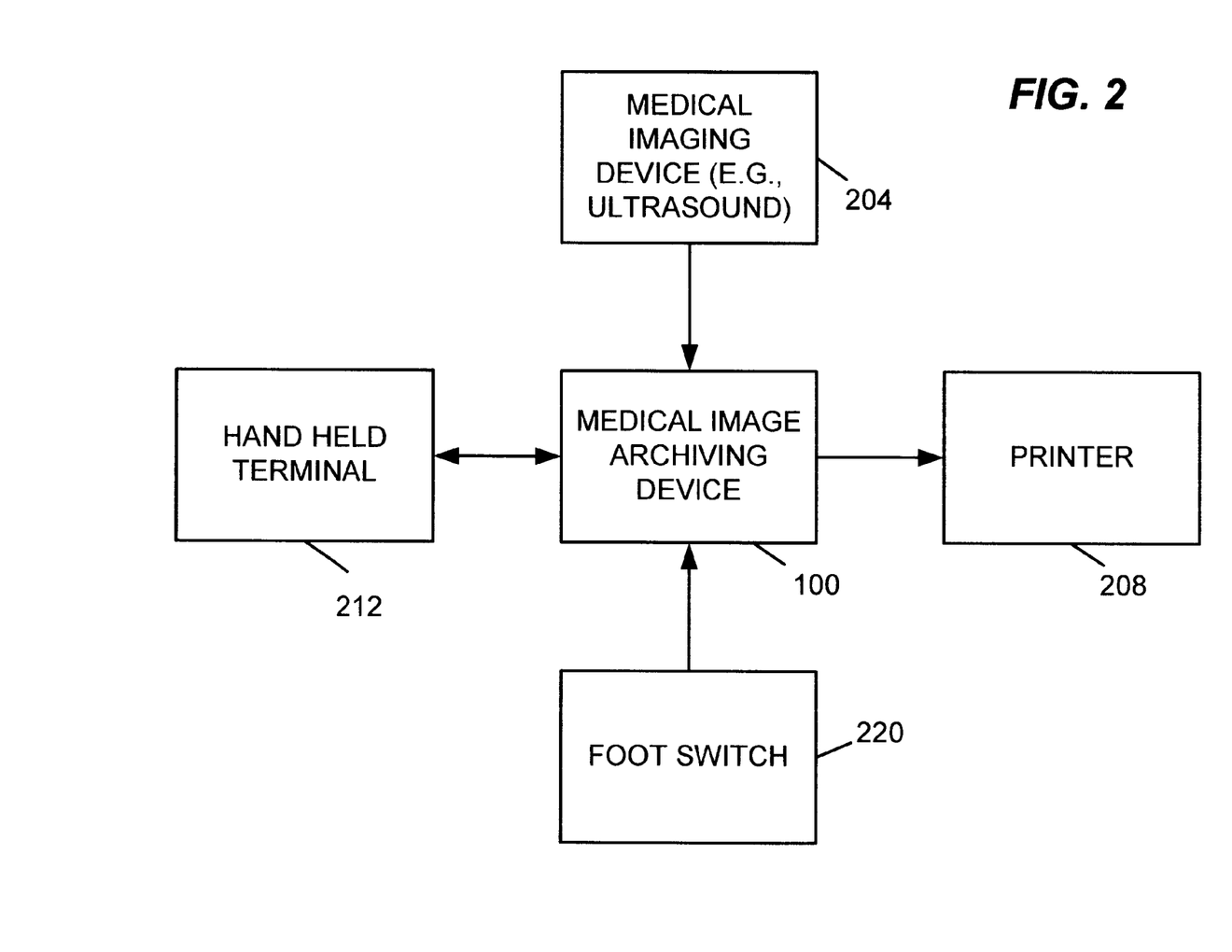
FIG. 2 illustrates a first exemplary system consistent with an embodiment of the present invention.

Referring now to FIG. 2 a first exemplary system 200 consistent with an embodiment of the present invention is illustrated including the image archiving device 100 connected to a medical imaging device 204 (e.g., an ultrasound device), a printer 210, a hand held terminal 212, and footswitch 220.

The medical image archiving device 100 uses an embedded PC based on processor 108 as a control processor to provide the following functionality. The medical image archiving device 100 receives an analog signal from the image capture device 204, stores the image in digital form at the internal hard disc drive 128 (perhaps temporarily) and outputs corresponding digital signals to the media writer 134 and the printer 210. The medical image archiving device 100 also receives image capturing and storing commands, preferably from a simplified foot operated device such as a three button serial footswitch 220, but may instead or in addition to the footswitch 220 utilize a keyboard and/or a display device, or hand held terminal 212 to facilitate input. Utilizing this functionality, the medical image archiving device 100 permits the user to capture the images (e.g., ultrasound images), print them using a high quality printer 210, record the images on a non-volatile storage medium such as a CD-R or DVD to facilitate organization, management and archiving of the images. Preferably, images stored on a CD are stored as a session with the CD being closed after writing the session to prevent further writing on the CD.

In accordance with a preferred embodiment, the stored images are indexed via a predictable syntax, whether the user enters specific information via a keyboard or hand held terminal 212 (e.g., patient and doctor names), or uses the image archiving device 100 without the keyboard or terminal 212. Use of a predictable syntax eases future management and retrieval of the images. In accordance with certain embodiments, if the user chooses not to have the keyboard or terminal 212 connected to the system, an "automatic indexing" mode is used.

The pictures are stored on the image archiving device 100's local hard disc drive 128 in a "session" format, one patient name being attached to a session. The sessions may be kept on local storage for any suitable period of time (e.g., 4 or 72 hours selectable) or until a user chooses to manually erase them. At convenient times (e.g., nightly) or at periodic intervals (e.g., every 72 hours erased and the disc storage freed for subsequent operation (e.g., the following morning). Preferably, the pictures will have been backed up onto a system server or other persistent storage prior to freeing the local storage.

Figure 3:
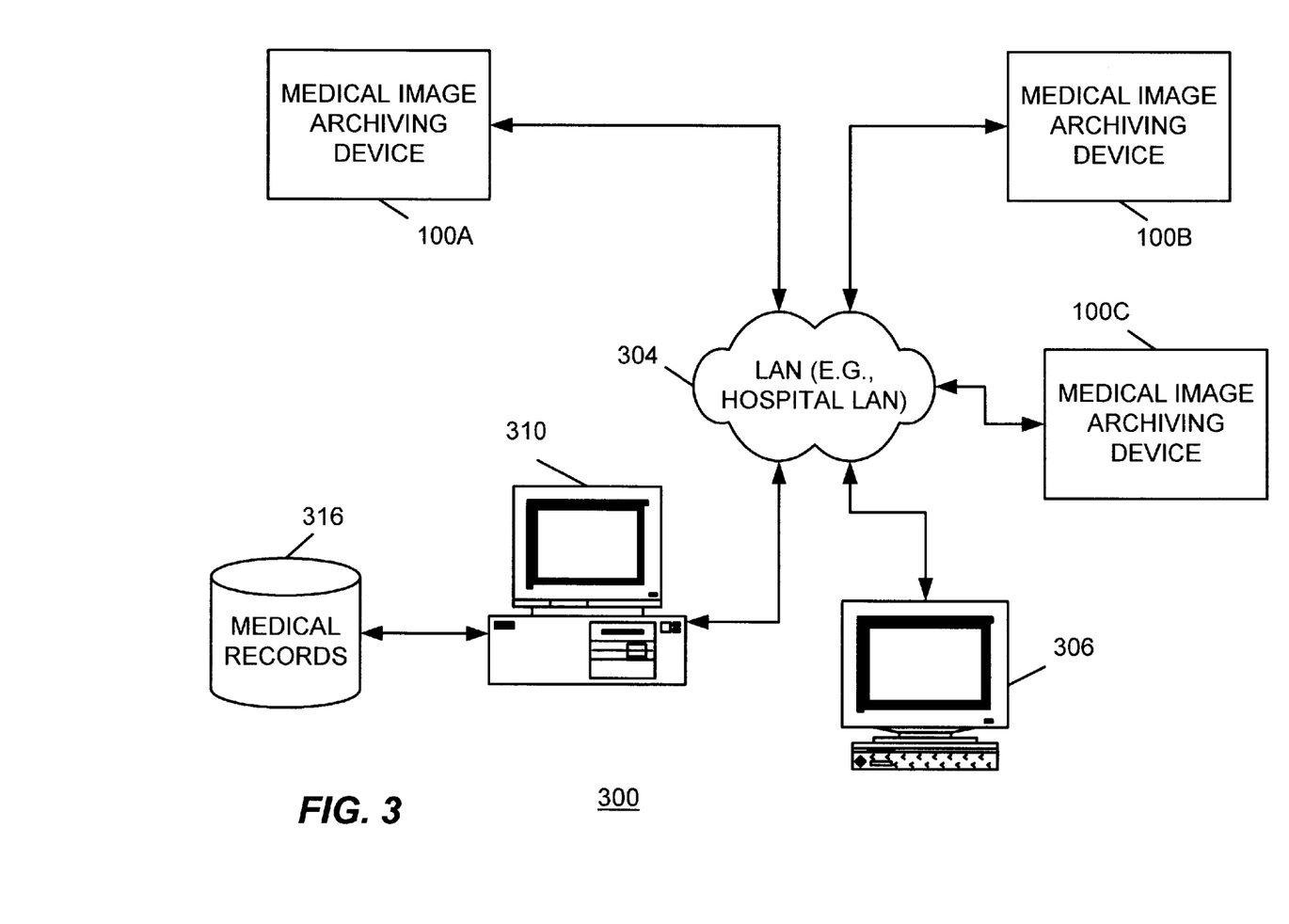
FIG. 3 illustrates a second exemplary system consistent with an embodiment of the present invention, using a hospital LAN including multiple image archiving devices connected to a server.

Referring now to FIG. 3, an exemplary system 300 is illustrated using a hospital LAN 304 used to network a plurality of medical image archiving systems 100A, 100B and 100C connected to various client terminal devices 306 and as well as a server 310 serving as a repository for a database of medical records 316. In such a system, medical records can be centrally stored in server 310's database 316 with input from any of the medical image archiving devices 100A, 100B and 100C periodically contributing to the storehouse of information. Any of this information may be retrieved at any time from a client workstation 306 or other appropriately connected viewing device connected to the LAN 304 for immediate access to the information. In this manner, consulting physicians can view images from their office, a library or any other convenient location having access to the hospital LAN 304 to provide more rapid and efficient viewing. Since the medical image archiving devices each incorporate the software that implements a web server, each has an IP address that can be used from any terminal to access the data stored on the disc drive 128 thereof using any suitable browser software.

Figure 4:
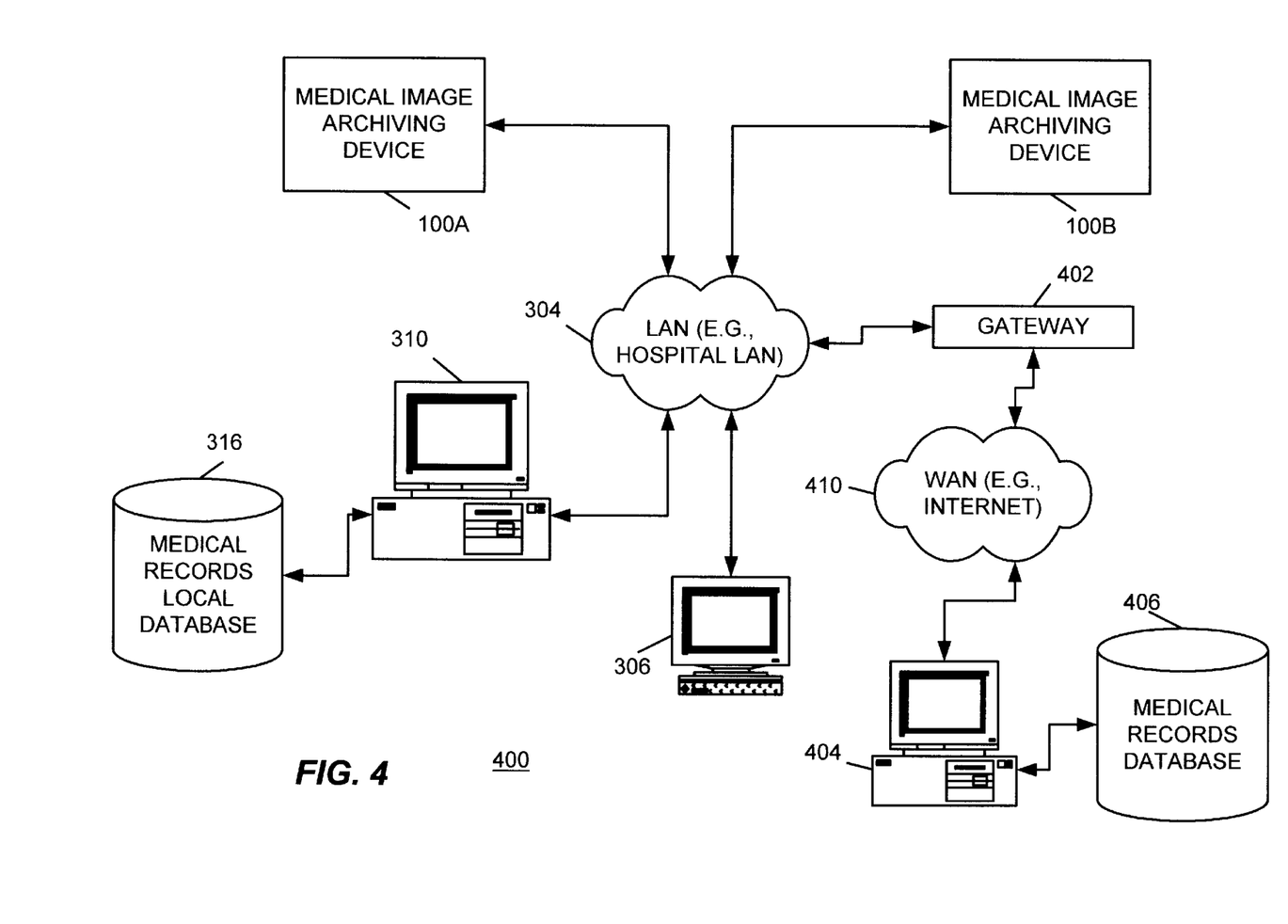
FIG. 4 illustrates a third exemplary system consistent with an embodiment of the present invention, in which a hospital server is connected to a records managing server through a public network such as the Internet.

FIG. 4 illustrates a third exemplary system consistent with an embodiment of the present invention, in which the hospital server 310 is connected via a gateway 402 to a records managing server 404 having a medical records database 406 through a public or private network 410 such as the Internet. In this embodiment, preferably, the hospital LAN 304 implements a web server. Pictures stored on the image archiving device hard disc drive 128 can be reviewed remotely via a TCP/IP connection, using a regular browser. Thus, an expert physician, technician or researcher in another city can be provided with access to view a particular patient's images (either on the local database 316 or on the medical image archiving devices 100A or 100B) without need for delays associated with mailing hard copy records for review. Security software 154, such as that commercially available from Verisign, 1350 Charleston Road, Mountain View, Calif. 94043 or others can be used to control access to the images. Pictures can be automatically downloaded and stored at the remotely located medical records management server 404 during evening hours or the like, before freeing the local storage as described above.

Additionally, the embodiment of FIG. 4 provides an easy way to dynamically setup the image archiving device 100. The settings for the device can be made directly upon set up, using the optional keyboard/LCD. Alternatively, the settings can be remotely provided at the hospital server 310, client node 306 or any other appropriate node, using a browser based interface, such as the commercially available Netscape Navigator™, from Netscape, 466 Ellis Street, Mountain View, Calif. 94043 or other browser software. The selectable settings in this embodiment include IP address, hospital/practice name, and storage length, and backup characteristics. Preferably, the medical image archiving device also includes a non-volatile flash memory forming a part of memory 112 that stores settings information. In addition to initialization, maintenance can be performed remotely via the network or the web.

Preferably, the hardware platform of the image archiving device includes a bookshelf type housing having a footprint of approximately 12"×12"; a conventional medical grade power supply; an Intel Pentium™ class processor (e.g., a processor compatible with and preferably having at least the processing power of an Intel Celeron™ 333 MHz microprocessor, available from Intel Corporation, Santa Clara, Calif.); 2 PCI expansion slots; one exposed bay for the recording device 216 (e.g., CD-R, CD-RW or DVD+RW (ATAPI)); hard drive 128 (e.g. 10 Gb); 32 Mb of RAM; a preferably 60 GB or greater hard disc drive; a network interface 140 (e.g. fast Ethernet); a conventional video based capture board including composite and Y/C inputs forming interface 104 and frame grabber interface card 104; and a SCSI interface card. Other configurations could also be used without departing from the present invention. For example, in another embodiment, all parts could be integrated into a single circuit board rather than using standard PC components.

The image archiving device 100 can be implemented using any suitable operating system. In the preferred embodiment, the Linux operating system is used to minimize cost by operating in a license free environment. The Linux system (e.g., Red Hat Linux version 6.0 or later, available from Red Hat, Inc., 2600 Meridian Parkway, Durham, N.C. 27713, running in a minimal configuration) can provide multitasking abilities and device support for the CD-burner and the video capture device. Although various additional components may be provided where space and or cost limitations are not present, the basic level image archiving device 100 need not necessarily require a display adapter (VGA), keyboard, network, or a floppy disc drive.

Preferably, much of the functionality of capturing, storing, writing, printing and communicating with other network nodes is provided by software, but hardware could also provide certain of the functionality. Generally the software modules would run on the Linux Operating system (e.g. Red Hat 6.0, minimum configuration), as described above. The software used in the present system can be broken into several modules. The operating system module may be embodied as Standard Red Hat Linux 6.0 (minimum configuration), and Linux printing subsystem (lpd, lpr, lpq, etc . . . ), for example. The main application module is responsible for monitoring the user input device (serial smart footswitch), triggering the frame grabber to catch the current image, printing in multiple formats (single image, 4 on 1, and 6 on 1—on single sheet), and transferring the image to the print subsystem for processing. A frame grabbing module incorporating a frame grabber device driver that drives the frame grabber board is used by the image archiving device 100 to handle image capture, and storage along with user interface functions. A footswitch module receives input from a smart footswitch connected via a keyboard interface. Preferably, three different events are triggered by the footswitch, although various configurations may be realized. The three events in one embodiment could be "grab image," "store image" and "print image." The software system may also include a copy protection module, a printer driver for any suitable printer such as the Sony™ printer UPD-70XR (SCSI and parallel). The printer driver integrates into the Linux printing subsystem, making the spooling and printing of the images transparent to the application. The software may also include a CD-R/W writing module that controls the function of a CD writer.

Figure 5:
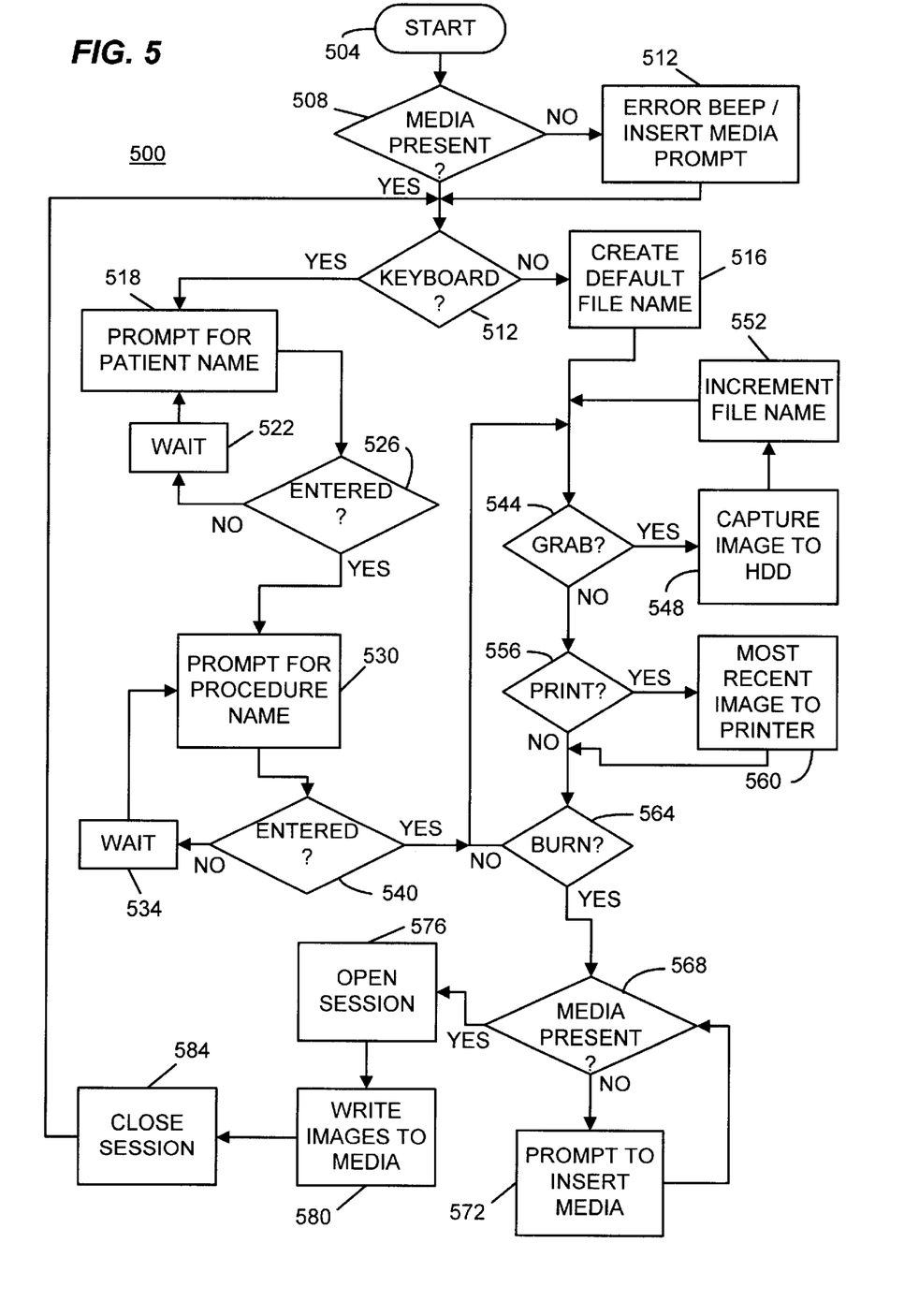
FIG. 5 is a flow chart illustrating an operational mode consistent with an embodiment of the present with a CD or DVD writer drive attached.

Referring now to FIG. 5, a process for operation of the image archiving device 100 with an attached CD writer 134 is described starting at 504. As part of an initialization process, a specific memory location is inspected where a hospital name/practice name should be kept. If this location is empty then the image archiving device 100 issues a warning sound (e.g., long beeps) and waits for a user to carry out a setup procedure. At this time a regular keyboard and computer display, or hand held terminal 212 should be attached either directly or via a network connection, according to the present embodiment, and the user should follow the instructions on the screen to perform the setup (hospital/practice name, date and time, IP address, etc.). At any time, the user can change the settings by connecting a regular PC keyboard and monitor and repeating the above setting procedure. This allows the user to change the names or the IP address in order to fit the needs. The setup can also be performed through the network from a terminal or server using the connection described above.

After the initialization process, the software checks for the presence of media (e.g., CD-R) in the media writer 134 at 508. If media is not present, a beep or other warning and prompt to the user to insert the media is issued at 512. If media is detected at 508, control passes to 512. The software checks at 512 for an installed keyboard and display or hand held terminal on a serial or keyboard port at 512. In accordance with one embodiment, a file name system is created by the software according to a default process at 516 if no input device is present at 512. If a keyboard or other input device is detected at 512, the user is prompted for a patient name at 518. The software then waits at 522 until the name is entered at 526. Once entered, the software prompts the user for the procedure name at 530 and waits at 534 until the name is entered at 540. Control then passes to 544 from either 540 or 516 to await the input (e.g., from a three switch foot switch 220) for commands to grab an image, print an image or burn a CD (or otherwise record to the media. In other embodiments, the user can be prompted for any information desired for creation of a file name.

According to the preferred embodiment, the file name is created from the operator input for patient name, followed by a sequential number (starting from number 001), a fixed hospital or practice name, time and date, optional operator keyboard input for performed procedure and a standard file extension at 528. Of course, other formats can be used without departing from the invention, and other information can be obtained by user input besides that explicitly described above. The template for the file name for this embodiment is:

---

"<Patient name>__<sequential image number >__<Hospital/practice name>__hh-mn-mm-dd-yyyy__<Optional Procedure>.tif"
Example:
"John Smith__001__St.George's Hospital__18-05-02-12-1997__kidney.tif"
The next image for the same patient might be:
"John Smith__002__St.George's Hospital__18-08-02-12-1997__kidney.tif"
The first image for the second patient:
"O'Connell Terry__001__St.George's Hospital__18-17-02-12-1997__knee.tif"

---

In the event a keyboard is not detected at 512, the file name is created according to a default algorithm at 516. In the preferred embodiment, the file name will start with a <Patient-001> followed by <sequential image number>, <Hospital/practice name>, <time and date> and a standard file extension. Since the operator will not input names, a default patient name is used. The default patient name in this embodiment is "Patient-001". The next patient name will be "Patient-002" and so on. At the end of the day, after cleaning up the buffer (hard disc drive 128), the default patient name may be reset to "Patient-001" in one embodiment or continue sequentially in others. Of course, other naming conventions can also be used without departing from the invention. The template for the present file naming convention is:

---

"<<Patient-001>__<sequential image number>__<Hospital/practice name>__<hh-mn-mm-dd-yyyy>.tif"
Example:
"Patient-001__001__St.George's Hospital__12-35-02-12-2000.tif"
The next image for the same patient will be:
"Patient-001__002__St.George's Hospital__12-40-02-12-2000.tif"
The first image for the second patient:
"Patient-002__001__St.George's Hospital__12-45-02-12-2000.tif"

---

The file names in the preferred embodiment should not exceed 256 characters including sequential number, hospital name, time stamp and procedure, but this should not be considered limiting. If the operator inputs more then 256 characters in this embodiment, input will be truncated in such a way that sequential number, hospital name and patient name will be kept intact. (Discarding characters from operator input to keep file name up to 256 characters).

At 544, if a grab command is received (e.g., by foot switch operation), the image from the imaging device is captured (grabbed) and saved to the hard disc drive 128 at 548. The file name is incremented at 552 and the software again awaits a foot switch or other input. If a Grab command is not received and the Print command is received at 556, then the most recently grabbed image is appropriately formatted and labeled and sent to the printer at 560. If a Burn command is received at 564, the software again inspects the media writer 134 for the presence of valid media. If there is no media present at 568 or the media is for some reason invalid or otherwise unusable, an error message is generated, preferably including a prompt to insert valid media at 572. In the case of a writeable CD, the images are written as a session. When valid media is detected at 568, a new session is opened on the CD at 576, the session is written at 580 and the session is closed at 584 and the media ejected. Similar processes can be used for other media. The process then returns to 512 to await the next imaging session. This embodiment assumes that the session is written as a batch. In other embodiments, the session can be written as the images are taken without departing from the invention.

If a valid blank CD is present at 568, the CD driver software module carries out the task of preparing the CD image on the hard drive into a standard ISO9660 file format required by the CD-R burning software (or any appropriate file format for writing on DVD+RW). The CD image is burned into the CD-R in single session mode, also known as CD-ROM mode-1 (or any appropriate file format for writing on DVD+RW). At the end of the write operation when the last image has been written the disk is "closed" not allowing any more sessions on the same media, and the media is ejected from the drive.

If the user presses the eject button or the unit is powered down while writing is in progress then the CD image remains on the hard disc drive 128 as well as the original images. At the next power up an audible signal warns the operator that a CD image is waiting to be transfer to the CD-R drive. At this time the operator can insert a blank disk in the drive and press an appropriate key to cause the CD image to be written to the CD-R. The operator can choose to ignore this warning by operating the unit in a usual manner; for example, input new patient name, and start capturing new images. In this case the unwritten CD image will be kept on the hard drive until the next hard drive clean up. Other error trapping can also be implemented without departing from the invention, however, the embodiment illustrated in FIG. 5 has been simplified to minimize such error trapping and other details so as not to obscure the invention.

The captured .tif or DICOM (or other format) images may be variously manipulated for printing, preferably to provide 1, 4, 6 or 9 image prints per page. One preferred printer is the Sony™ UP-D70XR photo-realistic printer—available commercially from Sony Corporation, Tokyo, Japan, which provides full letter-sized printing capabilities for various medical and scientific applications. The UP-D70XR includes a 300 dpi thermal head that prints in color images in approximately 55 seconds and transparency images in approximately 45 seconds. A gray balance calibrating function allows users to set the ideal gray balance for color accurate images. The print area covers up to 8"×10" on letter-size paper and full-bleed on A4+paper. The UP-D70XR includes SCSI and Centronics interface for connection to the image archiving device. For DICOM format, the UPA-D3 Digital Print Server can be used with this printer, and can communicate with the printer over the hospital LAN using TCP/IP. Of course, any suitable printer can be used without departing from the present invention.

The image archiving device 100 of the preferred embodiment has either a default "doctor" name, or has facilities for receiving doctor's names such as via a keyboard. The file directory organizes records into files denoted by the name of the doctor performing the procedure. So, if Doctor Gooden is performing the procedures on patient John Doe, then the captured images are stored in a folder called "Gooden", with each file in the folder incorporating a standard syntax including the patient's name, image number, hospital/practice name, time & date, and procedure information as described above. Thus, a doctor's files are easily located, as they are all stored together in a unique file.

In the network environment, with the browser based functionality as described above, various records can be easily accessed and managed, and the records can further be organized according to the above described syntax. That is, the records for a given doctor could be browsed, and HTML links to the individual files, for remote viewing, downloading and the like are readily provided. By virtue of the medical image archiving device being equipped with a web server, the device can be addressed by its IP address, queried to request a stored image, and transmit the stored image to an IP address associated with the request.

The described file storage syntax could be modified by the hospital or another entity. For example, each patient may be assigned a unique identifier, which might follow the patient as they receive treatment at various institutions. The medical records management server could store all of the records for that individual using the unique identifier. Alternatively, the medical records management server might provide a search engine for finding records based upon information such as the patient name, doctor name, hospital name, date, etc.

Figure 6:
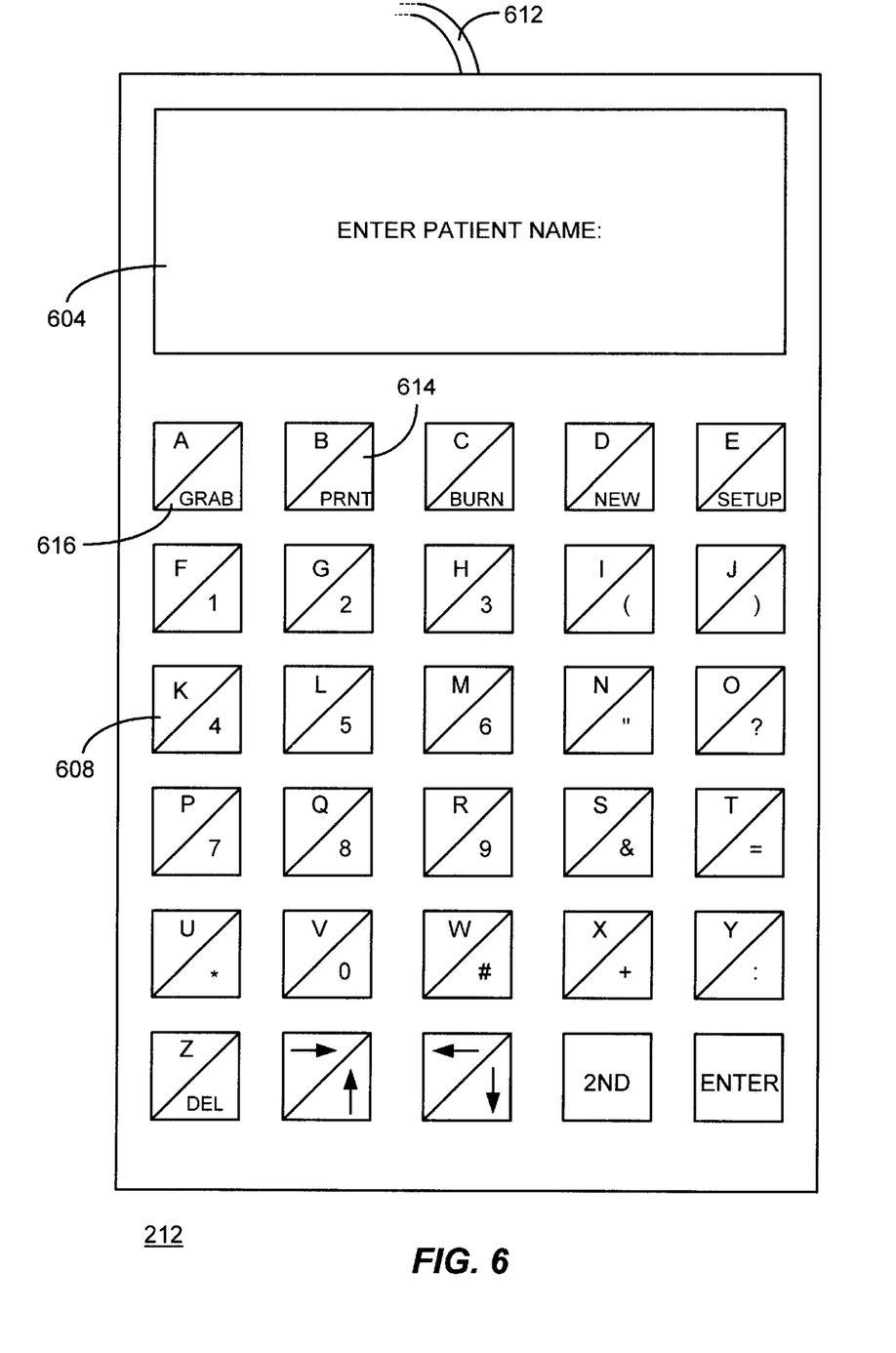
FIG. 6 is an illustration of a hand-held terminal suitable for use with an embodiment of the present invention.

Referring now to FIG. 6, an exemplary hand held terminal is illustrated. The terminal includes a small display 604 (e.g., an LCD display panel) with large enough resolution to permit display of all needed prompts and user inputs. Scrolling can be used if needed to facilitate display of prompts and user input. An array of input keys such as alpha-numeric key 608 is also provided to permit entry of text and numerical data. In one embodiment, specific function keys such as a "print" key 614 and a "grab" key 616 may be provided. In other embodiment, generic function keys (F1, F2, ...) are used. The hand held terminal 212 may be connected to the medical image archiving device 100 by a cable 612 or using infrared or other communications as will be evident to those skilled in the art. The specific keyboard layout shown is intended only to be exemplary and should not be considered limiting. Other terminal configurations can also be used.

Figure 7:
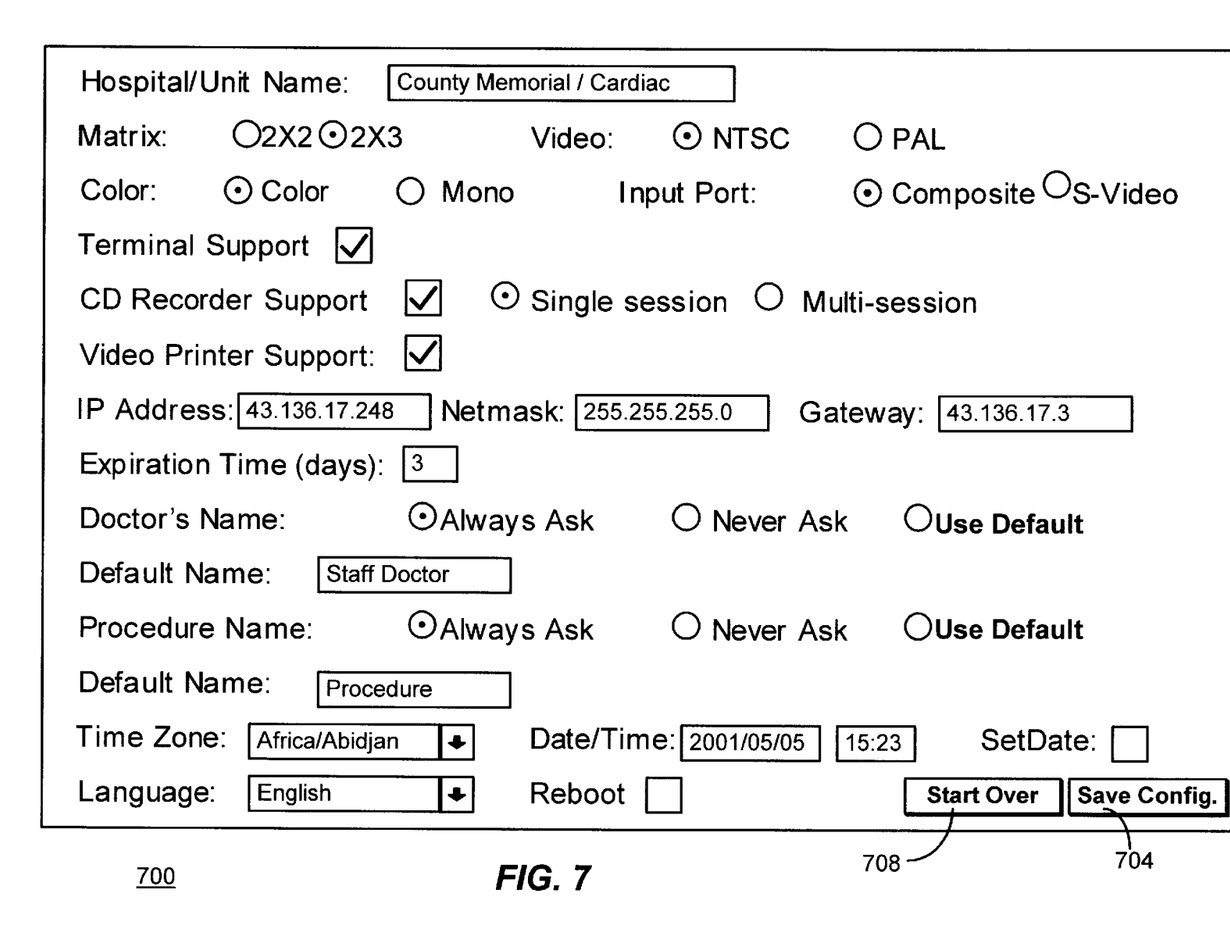
FIG. 7 illustrates an exemplary setup screen used in one embodiment consistent with the present invention.

FIG. 7 shows an exemplary setup screen used in the preferred embodiment of the invention. In this screen, various default and system parameters are entered and stored in flash memory, or other non-volatile storage for use by the device 100. When the medical image archiving device 100 is turned on for the first time, or when a specified command is issued to initiate a setup, a setup screen such as screen 700 appears. Screen 700 is created, in one embodiment, using HTML and is displayed using a browser. In a network embodiment, the setup screen can be displayed and completed from a remote terminal device such as 306. In this screen 700, the user can enter the number of prints per page (in this embodiment 2×2 or 2×3) and the type of video format being received. The user also selects the type of display (color or monochrome) and the input port being used (composite or S-Video).

The user can also select whether or not a terminal such as hand held terminal 212 is to be used or not and whether a CD Recorder is being supported (in either single session or Multi-session formats). The user also selects whether or not a printer is connected. In a networked situation, IP address, Netmask and Gateway identifiers are entered to permit communication over the network. The amount of time a file can remain on the hard disc drive 128 until purged can be entered as well as default procedure and doctor names. Whether or not the default names are used or whether the user is queried for names when used is entered also. The screen 700 also permits entry of date, time and time zone as well as language support. The user can also elect to set the date or reboot when the configuration is saved using the save configuration button 704. Errors can be corrected by starting over using start over button 708. Of course, those skilled in the art will understand that the screen 700 is intended to be exemplary and many variations and enhancements are possible within the scope of the present invention.

This invention allows those using analog imaging devices without storage and/or printing facilities to upgrade at reasonable cost to digital image archiving and managing operations and/or to implement convenient digital image back up storage and easy transportability of the image over local or wide area networks including the Internet. The invention also obviates the need for wet processing of silver halide film and the corresponding chemistry for production of printed images, making it an environmentally friendly and cost effective solution.

Those skilled in the art will recognize that the present invention has been described in terms of exemplary embodiments based upon use of a programmed processor. However, the invention should not be so limited, since the present invention could be implemented using hardware component equivalents such as special purpose hardware and/or dedicated processors which are equivalents to the invention as described and claimed. Similarly, general purpose computers, microprocessor based computers, microcontrollers, optical computers, analog computers, dedicated processors and/or dedicated hard wired logic may be used to construct alternative equivalent embodiments of the present invention.

Those skilled in the art will appreciate that the program steps used to implement the embodiments described above can be implemented using disc storage as well as other forms of storage including Read Only Memory (ROM) devices, Random Access Memory (RAM) devices; optical storage elements, magnetic storage elements, magneto-optical storage elements, flash memory, core memory and/or other equivalent storage technologies without departing from the present invention. Such alternative storage devices should be considered equivalents.

The present invention is preferably implemented using a programmed processor executing programming instructions that are broadly described above in flow chart form and can be stored on any suitable electronic storage medium. However, those skilled in the art will appreciate that the processes described above can be implemented in any number of variations and in many suitable programming languages without departing from the present invention. For example, the order of certain operations carried out can often be varied, and additional operations can be added without departing from the invention. Error trapping can be added and/or enhanced and variations can be made in user interface and information presentation without departing from the present invention. Such variations are contemplated and considered equivalent.

While the invention has been described in conjunction with specific embodiments, it is evident that many alternatives, modifications, permutations and variations will become apparent to those skilled in the art in light of the foregoing description. Accordingly, it is intended that the present invention embrace all such alternatives, modifications and variations as fall within the scope of the appended claims.

What is claimed is:

1. A medical imaging method in a medical image archiving device, comprising:
   sending a prompt for image identification information to a hand held terminal;
   receiving the image identification information from the hand held terminal;
   receiving a grab image command from one of a footswitch and the hand held terminal;
   receiving an analog video input signal from a medical imaging device;
   converting a frame of the analog video input signal to a digital representation within the image archiving device in response to receiving the grab image command from one of the footswitch and the hand held terminal;
   receiving a store image command from one of the footswitch and the hand held terminal;
   assigning a file name to the digital representation based on the image identification information;
   storing the digital representation on a disc drive;
   receiving a burn CD command from one of the footswitch and the hand held terminal: and
   storing the digital representation as a part of a session on an optical storage medium.

2. The method according to claim 1, further transmitting the digital representation over a communication network to an IP address.

3. The method according to claim 1, further comprising transmitting the digital representation over a local area network to an electronic storage device.

4. The method according to claim 1, further comprising transmitting the digital representation over a wide area network to an electronic storage device.

5. The method according to claim 4, wherein the wide area network comprises the Internet.

6. The method according to claim 1, wherein the digital representation comprises one of a .tiff format digital representation and a DICOM (digital imaging and communications in medicine) format digital representation.

7. The method according to claim 1, wherein the analog video input signal is formatted in one of PAL and NTSC format video.

8. The method according to claim 1, further comprising detecting whether the hand held terminal is available, and assigning a default file name if the hand held terminal is not present.

9. The method according to claim 8, further comprising generating assigning a default file name if no input device is available.

10. A medical image archiving system, comprising:
    a footswitch;
    a hand held terminal; and
    a medical image archiving device, comprising:
      an interface for attaching the footswitch;
      an interface for attaching the hand held terminal;
      a frame grabber receiving an analog video image from a medical imaging device and producing a digitized still image in response to a grab image command from one of the footswitch and the hand held terminal;
      a programmed processor;
      a network interface adapter that interfaces the processor to an electronic communication network;
      a web server application running on the programmed processor, the web server having an IP address associated therewith;
      a disc drive that stores the digitized still image in response to a store image command received from one of the footswitch and the hand held terminal;
      an application program running on the programmed processor that receives a request directed to the IP address for the digitized still image from the network via the network interface adapter, and generates a reply transmitting the digitized image to an IP address associated with the request.

11. The apparatus according to claim 10, wherein the application program transmits the digitized still image to an electronic storage device.

12. The apparatus according to claim 11, wherein the digital image is transmitted over one of a local area network and a wide area network.

13. The apparatus according to claim 10, wherein the wide area network comprises the Internet.

14. The apparatus according to claim 10, wherein the digital representation comprises one of a .tiff format digital representation and a DICOM (digital imaging and communications in medicine) format digital representation.

15. The apparatus according to claim 10, wherein the analog video input signal is formatted in one of PAL and NTSC format video.

16. The apparatus according to claim 10, wherein the application program detects whether the hand held terminal is available, and assigns a default file name if the hand held terminal is not connected to the interface for attaching the hand held terminal.

17. The apparatus according to claim 16, wherein the application program assigns a default file name if no input device is connected to the interface.

18. The apparatus according to claim 10, further comprising a CD writer, and wherein the application writes the digitized image to a CD using the CD writer as a session.

19. The apparatus according to claim 18, wherein the application closes the CD after writing the session to the CD.

20. A storage medium storing instructions which, when executed on a programmed processor in a medical image archiving device, carry out a process of:
    sending a prompt for image identification information to a hand held terminal;
    receiving the image identification information from the hand held terminal;

receiving a grab image command from one of a footswitch and the hand held terminal;

receiving an analog video input signal from a medical imaging device;

converting a frame of the analog video input signal to a digital representation within the image archiving device in response to receiving the grab image command from one of the footswitch and hand held terminal;

receiving a store image command from one of the footswitch and the hand held terminal;

assigning a file name to the digital representation based on the image identification information;

storing the digital representation on a disc drive;

receiving a burn CD command from one of the footswitch and the hand held terminal; and storing the digital representation as a part of a session on an optical storage medium.

21. The method according to claim 19, further comprising transmitting the digital representation over one of a wide area network and a local area network.

* * * * *

UNITED STATES PATENT AND TRADEMARK OFFICE
CERTIFICATE OF CORRECTION

PATENT NO. : 6,678,764 B2
DATED : January 13, 2004
INVENTOR(S) : Parvulescu et al.

It is certified that error appears in the above-identified patent and that said Letters Patent is hereby corrected as shown below:

Column 4,
Line 65, after "hours", insert -- the pictures are --.

Column 11, line 24 - Column 14, line 9,
Delete all claims and replace with the following claims:

1. A medical imaging method in a medical image archiving device, comprising:
   detecting whether a hand held terminal is available;
   if the hand held terminal is available, sending a prompt for image identification information to the hand held terminal;
   if the hand held terminal is available, receiving the image identification information from the hand held terminal;
   receiving a grab image command from one of a footswitch and the hand held terminal;
   receiving an analog video input signal from a medical imaging device;
   converting a frame of the analog video input signal to a digital representation within the image archiving device in response to receiving the grab image command from one of the footswitch and the hand held terminal;
   receiving a store image command from one of the footswitch and the hand held terminal;
   assigning a file name to the digital representation based on the image identification information, wherein, the file name comprises a default file name if the hand held terminal is not available;
   storing the digital representation on a disc drive;
   receiving a burn CD command from one of the footswitch and the hand held terminal; and
   storing the digital representation as a part of a session on an optical storage medium.
2. The method according to claim 1, further transmitting the digital representation over a communication network to an IP address.
3. The method according to claim 1, further comprising transmitting the digital representation over a local area network to an electronic storage device.
4. The method according to claim 1, further comprising transmitting the digital representation over a wide area network to an electronic storage device.
5. The method according to claim 4, wherein the wide area network comprises the Internet.
6. The method according to claim 1, wherein the digital representation comprises one of a .tiff format digital representation and a DICOM (digital imaging and communications in medicine) format digital representation.
7. The method according to claim 1, wherein the analog video input signal is formatted in one of PAL and NTSC format video.
8. The method according to claim 1, further comprising generating assigning a default file name if no input device is available.
9. A medical image archiving system, comprising:
   a footswitch;
   a medical image archiving device, comprising:
      an interface for attaching the footswitch;
      an interface for attaching a hand held terminal;
      a frame grabber receiving an analog video image from a medical imaging device and producing a digitized still image in response to a grab image command from one of the footswitch and the hand held terminal;
      a programmed processor;
      a network interface adapter that interfaces the processor to an electronic communication network;
      a web server application running on the programmed processor, the web server having an IP address associated therewith;
      a disc drive that stores the digitized still image in response to a store image command received from one of the footswitch and the hand held terminal; and
      an application program running on the programmed processor that receives a request directed to the IP address for the digitized still image from the network via the network interface adapter, and generates a reply transmitting the digitized image to an IP address associated with the request, and wherein the application program detects whether the hand held terminal is connected to the interface for connecting the hand held terminal, and assigns a default file name if the hand held terminal is not connected to the interface for attaching the hand held terminal.
10. The apparatus according to claim 9, wherein the application program transmits the digitized still image to an electronic storage device.

UNITED STATES PATENT AND TRADEMARK OFFICE
CERTIFICATE OF CORRECTION

PATENT NO. : 6,678,764 B2
DATED : January 13, 2004
INVENTOR(S) : Parvulescu et al.

It is certified that error appears in the above-identified patent and that said Letters Patent is hereby corrected as shown below:

Column 11, line 24 - Column 14, line 9 (cont'd),

11. The apparatus according to claim 10, wherein the digital image is transmitted over one of a local area network and a wide area network.
  12. The apparatus according to claim 9, wherein the wide area network comprises the Internet.
  13. The apparatus according to claim 9, wherein the digital representation comprises one of a .tiff format digital representation and a DICOM (digital imaging and communications in medicine) format digital representation.
  14. The apparatus according to claim 9, wherein the analog video input signal is formatted in one of PAL and NTSC format video.
  15. The apparatus according to claim 9, wherein the application program assigns a default file name if no input device is connected to the interface.
  16. The apparatus according to claim 9, further comprising a CD writer, and wherein the application writes the digitized image to a CD using the CD writer as a session.
  17. The apparatus according to claim 16, wherein the application closes the CD after writing the session to the CD.
  18. A storage medium storing instructions which, when executed on a programmed processor in a medical image archiving device, carry out a process of:
    determining if a hand held terminal is connected to the medical image archiving device;
    if the hand held terminal is connected, sending a prompt for image identification information to a hand held terminal;
    if the hand held terminal is connected, receiving the image identification information from the hand held terminal;
    receiving a grab image command from one of a footswitch and the hand held terminal;
    receiving an analog video input signal from a medical imaging device;
    converting a frame of the analog video input signal to a digital representation within the image archiving device in response to receiving the grab image command from one of the footswitch and hand held terminal;
    receiving a store image command from one of the footswitch and the hand held terminal;
    assigning a file name to the digital representation based on the image identification information, wherein the file name comprises a default file name if the hand held terminal is not connected;

storing the digital representation on a disc drive;
    receiving a burn CD command from one of the footswitch and the hand held terminal; and
    storing the digital representation as a part of a session on an optical storage medium.
  19. The method according to claim 18, further comprising transmitting the digital representation over one of a wide area network and a local area network.

Signed and Sealed this

Twenty-fourth Day of August, 2004

JON W. DUDAS
*Director of the United States Patent and Trademark Office*